US006365382B1

(12) United States Patent
Kranjc et al.

(10) Patent No.: US 6,365,382 B1
(45) Date of Patent: Apr. 2, 2002

(54) BIOTECHNOLOGICAL PROCESS FOR PREPARING HYDROXYLATED ML-236B DERIVATIVES, KNOWN AS M-4 AND M-4', AND ANALOGUES THEREOF

(75) Inventors: Sašo Kranjc, Ljubljana; Irena Ivanc, Radomlje; Manica Schauer, Ljubljana, all of (SI)

(73) Assignee: LEK Pharmaceuticals and Chemical Company D.D., Verovskova (SI)

( * ) Notice: Subject to any disclaimer, the term of this patent is extended or adjusted under 35 U.S.C. 154(b) by 0 days.

(21) Appl. No.: 09/700,945
(22) PCT Filed: May 21, 1999
(86) PCT No.: PCT/IB99/00923
§ 371 Date: Dec. 27, 2000
§ 102(e) Date: Dec. 27, 2000
(87) PCT Pub. No.: WO99/60151
PCT Pub. Date: Nov. 25, 1999

(30) Foreign Application Priority Data

May 21, 1998  (SI) ................................ 9800144

(51) Int. Cl.[7] .................................. C12P 7/62
(52) U.S. Cl. .................... 435/135; 435/125; 435/252.1; 435/253; 435/253.5; 435/872; 435/146; 424/305; 544/292; 549/292; 560/119; 560/188; 560/256
(58) Field of Search ................ 435/125, 135, 435/146, 252.1, 253, 253.5, 872; 424/305; 544/292; 549/292; 560/119, 188, 256

(56) References Cited

U.S. PATENT DOCUMENTS

| 4,346,227 A | 8/1982 | Terahara et al. ............ 560/119 |
| 4,410,629 A | 10/1983 | Terahara et al. ............ 435/146 |
| 4,537,859 A | 8/1985 | Terahara et al. ............ 435/146 |
| 4,547,488 A | 10/1985 | Merkel ........................ 514/10 |
| 5,153,124 A | 10/1992 | Furuya et al. ............... 435/125 |

FOREIGN PATENT DOCUMENTS

| EP | 0 649 907 A1 | 4/1995 | ............. C12P/7/02 |
| GB | 1 555 831 | 11/1979 | ........... C07C/69/74 |

OTHER PUBLICATIONS

Gherma et al. ATCC–Catalogue of Bacteria and Phages, American Type Culture Collection, p. 26 (1992).
McIntyre et al. Vancomycin Production in Batch and Continuous Culture, Biotechnology and Bioengineering, vol. 49, pp. 412–420 (1996).
Boeck et al. N–Demethylvancomycin, A Novel Antibiotic Produced by a Strain of Nocardia Orientalis Taxonomy and Fermentation, The Journal of Antibiotics, vol. 37, pp. 446–453 (1984).
PCT/IB 99/00923 International Search Report.

Primary Examiner—Leon B. Lankford, Jr.
Assistant Examiner—Kailash C. Srivastava
(74) Attorney, Agent, or Firm—Bromberg & Sunstein LLP

(57) ABSTRACT

The very effective conversion of ML-236B substances and derivatives thereof into 6'-hydroxylated products with the microorganisms of species *Amycolatopsis orientalis*, or with an extract or a hydroxylation-effective enzyme derived from said microorganism, is described. The products obtained are suitable as HMG-CoA reductase inhibitors or intermediates thereof. Thus, the products can be used, for example, as an antihypercholesterolemic in pharmacy.

12 Claims, No Drawings

BIOTECHNOLOGICAL PROCESS FOR PREPARING HYDROXYLATED ML-236B DERIVATIVES, KNOWN AS M-4 AND M-4', AND ANALOGUES THEREOF

Conventionally, the preparation of pharmaceutically acceptable salts of the HMG-CoA reductase inhibitors, such as the M4 and M-4' substances, is a fed-batch process. The first part comprises preparation of a ML-236B substance by fermentation with microorganisms of the genus Penicillium and its isolation using conventional isolation techniques and preparation of the sodium salt thereof as described in U.S. Pat. No. 4,137,322. The second part comprises cultivation of a microorganism of one of the aforementioned genera in the medium to which ML-236B, typically in the form of sodium salt is added, isolation of the M-4 and M-4' substances and optionally preparation of pharmaceutically acceptable salts thereof as disclosed in U.S. Pat. No. 4,346,227 and U.S. Pat. No. 4,537,859.

TECHNICAL FIELD

The present invention relates to a novel process for preparing hydroxylated ML-236 B derivatives, known as M-4 and M-4', and analogues thereof, in particular to an enzymatic hydroxylation by means of a microbiological process.

PRIOR ART

ML-236B and derivatives thereof as well as analogues are known as HMG-CoA reductase inhibitors and are disclosed in GB Pat. No. 1,555,831. They are produced by fermentation with various microorganisms of the genera Gilbertella, Streptomyces, Circinella, Monascus, Nocardia, Amycolata, Mucor or Penicillium (as disclosed in U.S. Pat. No. 4,346, 227 and U.S. Pat. No. 4,537,859). U.S. Pat. No. 5,153,124 describes the hydroxylation of a ML-236 B derivative by employing microorganisms of the genus Streptomyces or Amycolata. In EP 0 649 907 A1 the use of various microorganisms is disclosed, including *Amycolatopsis mediterranei* (ATCC 21411) among many other microorganisms. The hydroxylated forms of ML-236B, its derivatives and analogues, especially those

DESCRIPTION OF THE INVENTION AND THE PREFERRED EMBODIMENTS

The object of the invention has been solved by the provision of a process for preparing a compound defined by the following formula (I)

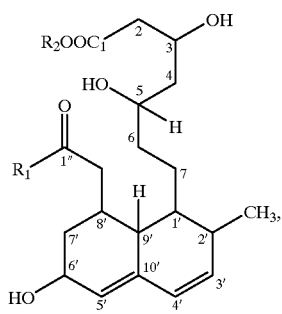

(I)

wherein $R_1$ represents substituted or unsubstituted alkyl or substituted or unsubstituted aryl, and $R_2$ independently represents H, substituted or unsubstituted alkyl or a cation;

or the corresponding lactone (II)

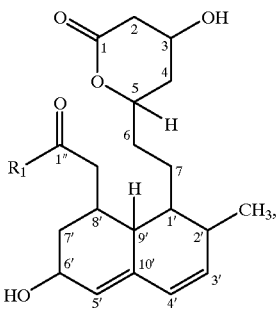

(II)

wherein $R_1$ is as defined above; of formula (I) or the corresponding lactone (II) with the microorganism *Amycolatopsis orientalis*, especially the strain deposited as ATCC 19795, in a suitable fermentation medium.

A fermentation medium should preferably comprise a source of assimilable carbon, such as glucose, saccharose, dextrins, glycerol, starch, soybean oil and molasses, a source of assimilable nitrogen, such as soybean flour, meat and yeast extracts, peptones, ammonium salts and, if required, various inorganic salts, such as sodium chloride, potassium chloride, magnesium sulphate, calcium carbonate and phosphates. Most conventional culture media may be used that employ microorganisms of the genus Amycolatopsis for fermentation. Suitable inoculation and fermentation media are, for example, described by J. J. McIntyre et al. in Biotechnology and Bioengineering, vol. 49, pp. 412–420 (1996); L. D. Boeck et al. in The Journal of Antibiotics, Vol. XXXVII No. 5, pp. 446–453 (1984); G. J. Clark et al. in Microbiology, Vol. 141, Pt. 3, pp. 663–669 (1995); and in U.S. Pat. No. 4,547,488; all descriptions being incorporated herein by way of reference.

Fermentation is carried out under aerobic conditions and at a temperature within a suitable range, for example from 20° to 36° C., preferably from 24° to 30° C. The aforementioned substrate compound to be hydroxylated may be contacted with the microorganism, preferably in the form of sodium salt, at any time in the course of fermentation or after completion of the fermentation, but an addition at the vegetative part of fermentation, which is normally between 24 and 48 hours after beginning cultivation, is particularly preferred. The compound substrate is added to a total final concentration of 0.01 wt.-% to 5 wt.-%, preferably 0.05 wt.-% to 0.5 wt.-%, based on the total fermentation broth weight or the contacting liquid. Addition to a fermentation medium may be either batch, fed-batch or continuous. Fermentation is usually completed within 2 to 5 days after addition of the substrate compound. Then, the microorganism cells are separated, preferably by filtration, and the resulting filtrate is extracted with an organic solvent which is preferably water immiscible or has a limited miscibility with water, such as ethyl acetate, ether (for example diethyl ether) or chloroform. Subsequently, the organic solvent is removed, suitably by evaporation, and if desired the resulting crude product is subjected to further conventional purification and isolation processes, for example employing column chromatography, e.g. using silica gel column, and eluting the desired compound with and appropriate eluent. If required, the resulting product may be subjected to recrystallization, salification (if it is desired in the form of a salt), lactonization or esterification, with methods known to those skilled in the art.

The product obtained by the microbiological process is typically a mixture of both 6'-hydroxy α- and β-configurations and can be used as such. If desired, the isomers with the respective α- and β-configuration may be separated by an appropriate isomer resolution technique known to those skilled in the art.

The structural moieties of R, and $R_2$ can be selected from the definitions as specified above for obtaining HMG-CoA reductase inhibitors or intermediates thereof. Thus, $R_1$ may represent optionally substituted alkyl or optionally substituted aryl. The alkyl group include straight chain, branched or cyclic hydrocarbon optionally having unsaturated double bonds and optionally being substituted. The main chain of the alkyl group has 1 to 15, preferably 1 to 10 and more preferably 1 to 6 carbon atoms, such as methyl, ethyl, propyl, isopropyl, butyl, isobutyl, t-butyl, pentyl, hexyl, the isomers and the branched derivatives thereof, and the like. The optional substituents include one or more of the group consisting of halogen such as chloro, amino, lower alkyl amino such as mono- or dimethylamino, hydroxy, alkoxy, cyano, nitro, and the like. A preferred substituent is hydroxy. If present, a branching hydrocarbon group preferably has 1 to 4 carbon atoms, such as methyl and ethyl. Possible aryl residues include substituted or unsubstituted phenyl, biphenyl and naphthyl,

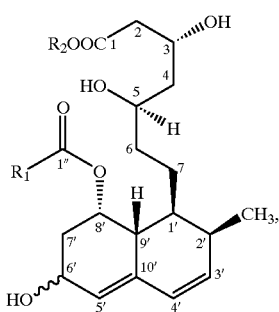

(Ia)

or the corresponding lactone compound (IIa); wherein $R_1$ and $R_2$ are as defined above, and the 6'∼∼OH—group represents an α- or a β-configuration, or a mixture of both α- and β-configurations. The compounds of formula (Ia) or (IIa) are obtained by starting with a 6'-H analogue having the corresponding configuration.

A particularly preferred example for $R_1$ is an alkyl residue having the following structure and configuration:

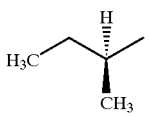

In a specifically preferred embodiment of the present invention, a compound having the following formula (III) or the salt thereof or the corresponding lactone is prepared in order to provide a particularly active and potent HMG-CoA reductase inhibitor or an intermediate thereof: for the prevention and/or treatment of diseases. The compounds obtained by the process according to the present invention, or the HMG-CoA reductase inhibitors derived therefrom, can be effectively used as an antihyper-cholesterolemic agent. The compounds can therefore be used for the preparation of a medicament for the control of cholesterol in the body of an individual. They can further be used for the prevention or the treatment of atherosclerosis. The obtained inhibitors and pharmaceuticals are particularly useful as preventives for reducing the risk of stroke, transient ischemic attack and myocardial infarction.

This invention is illustrated but in no way limited by the following examples.

EXAMPLE 1

Preparation of the Inoculum

The rationale for determining the most suitable productive culture was selection of individual colonies with the typical morphological characteristics. The selected colonies were transferred to a sterile potter to agar slopes and homogenized. The resulting colonies were transferred to agar slopes and incubated in the thermostat at 26° C. to 30° C. for 7 to 14 days. During that time surfaces of agar slopes were overgrown by a culture of homogeneous, folded, smooth, white to pale greyish-blue mycelium. A portion (0.5 to 1 ml) of the resulting culture was then inoculated into a vegetative medium.

EXAMPLE 2

Conversion of a ML-236B substance into 6'-Hydroxy Derivatives M-4 and M-4' Thereof A portion of the culture, prepared according to the method described in Example 1, was transferred into Erlenmeyer flasks with fermentation medium 1 to which a ML-236B substance having the formula shown below, in the form of sodium salt, was added to a concentration of 200 mg/L on the second day of fermentation. Analyses of the concentration of the 6'-hydroxylated M-4 and M-4' compounds in the fermentation broth showed the total final concentration of the M-4 and M-4' substances in the fermentation broth to be 60 mg/ml after 3 days of fermentation at temperature between 24° C. and 30° C.

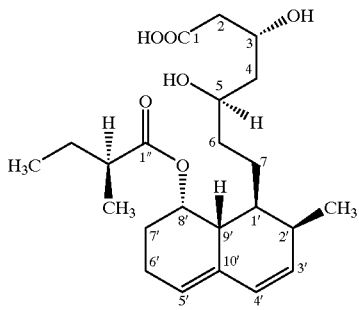

| Fermentation medium 1 | |
|---|---|
| Raw material | Amount |
| Glycerol | 80 g |
| Soybean flour | 20 g |
| Soybean oil | 0.1 g |
| Calcium gluconate | 12 g |
| Magnesium chloride × 6 $H_2O$ | 1.3 g |
| Magnesium sulphate × 7 $H_2O$ | 1 g |
| $NaNO_3$ | 10 g |
| Tap water to 1000 ml | |

All raw materials were dissolved in tap water, the pH was then adjusted to a value of 7.8 by addition of 1M aqueous solution of NaOH. The resulting medium was poured into 300 ml-Erlenmeyer flasks, 30 ml per flask.

EXAMPLE 3

Conversion of a ML-236B Substance into 6'-Hydroxy Derivatives M-4 and M-4' Thereof A portion of the culture, prepared according to the method described in Example 1, was transferred into Erlenmeyer flasks with fermentation medium 3 to which ML-236B, in the form of sodium salt, was added to a concentration of 400 mg/L on the second day of fermentation. Analyses of the concentration of M-4 and M-4' substances in the fermentation broth showed the total final concentration of the M-4 and M-4' substances in the fermentation broth to be 160 mg/ml after 3 days of fermentation at temperature between 24° C. and 30° C., indicating a 40% conversion.

| Fermentation medium 3 | |
|---|---|
| Raw material | Amount |
| Glycerol | 20 g |
| Soybean flour | 20 g |
| Calcium gluconate | 12 g |
| Magnesium chloride × 6 H$_2$O | 1.3 g |
| Magnesium sulphate × 7 H$_2$O | 1 g |
| NaNO$_3$ | 10 g |
| Tap water to 1000 ml | |

All raw materials were dissolved in tap water, the pH was then adjusted to a value of 7.8. The resulting medium was poured into 300 ml-Erlenmeyer flasks, 30 ml per flask.

EXAMPLE 4

Conversion of a ML-236B Substance into 6'-Hydroxy Derivatives Mi-4 and M-4' Thereof at Pilot Plant Scale The contents of ten Erlenmeyer flasks with the culture, prepared according to the method described in Example 1, whereas the vegetative part of fermentation was shorten to 24 hours, were used to inoculate the fermenter (14 l) with 10 of fermentation medium. After 24-hour fermentation, ML-236B, in the form of sodium salt (470 mg of ML-236B dissolved in 500 ml of water) was continually added to the medium for 6 hours. Analyses of the concentration of M-4 and M-4' substances in the fermentation broth showed the total final concentration of the M-4 and M-4' substances in the fermentation broth to be 300 mg after 36 hours of fermentation at temperature between 24° C. and 30° C., indicating a 64% conversion.

| Fermentation medium 2 | |
|---|---|
| Raw material | Amount |
| Glycerol | 20 g |
| Corn starch for fermentation | 20 g |
| Soybean flour for fermentation | 14 g |
| Glucose | 10 g |
| Yeast extract | 5 g |
| NaH$_2$PO$_4$ × 2 H$_2$O | 3.3 g |
| Tap water to 1000 ml | |

All raw materials were dissolved in tap water, the pH was then adjusted to a value of 7.8.

What is claimed is:

1. A process for preparing a compound defined by the following formula (I)

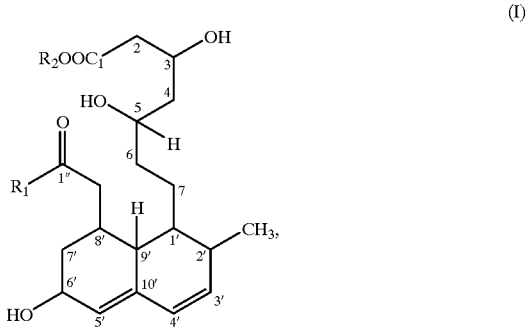

wherein $R_1$ represents substituted or unsubstituted alkyl or substituted or unsubstituted aryl, and $R_2$ independently represents H, substituted or unsubstituted alkyl or a cation;

or the corresponding lactone (II)

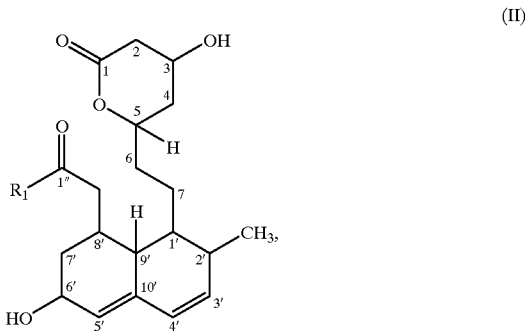

wherein $R_1$ is as defined above;

which process comprises contacting a 6'-H analogue of the above formula (I) or (II) for hydroxylation with a microorganism of the species *Amycolatopsis orientalis*.

2. A process according to claim 1, wherein the prepared compound of formula (I) has the following configuration (Ia):

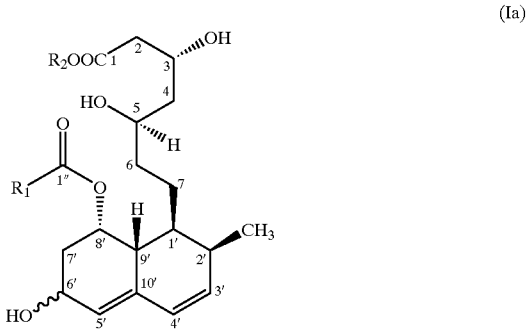

or the corresponding lactone compound (IIa);

wherein $R_1$ and $R_2$ are as defined in claim 1, the group 6'∼OH represents an α- or a β-configuration, or a mixture of both α- and β-configurations.

3. A process according to claim 1, wherein $R_2$ represents H, a $C_1$–$C_6$ alkyl group or a cation selected from the group consisting of an alkali metal, an ammonium group or an alkyl ammonium group.

4. A process according to claim 1, wherein $R_1$ represents an alkyl residue having the following structure:

wherein $R_3$ denotes H or $CH_3$ and $R_4$ independently denotes H or OH.

5. A process according to claim 4, wherein said alkyl residue has the following structure and configuration:

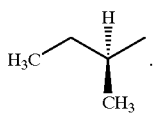

6. A process according to claim 1, wherein a compound having the following formula (III) or the salt thereof or the corresponding lactone is prepared:

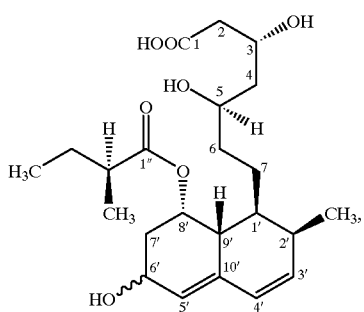

(III)

wherein the 6' ∼∼∼OH-group represents an α- or a β-configuration, or a mixture of both α- and β-configurations.

7. A process according to claim 1, wherein said microorganism is *Amycolatopsis orientalis* ATCC 19795.

8. A process according to claim 1, wherein said contacting step is performed in the course of fermentation of said microorganism, and wherein sand 6'-H analogue is added to the fermentation broth in a batch, feed-batch or continuous manner.

9. A process according to claim 8, wherein said 6'-H analogue is added to the fermentation medium to the final content of 0.05 to 0.5 wt.-%, based on the total medium weight.

10. A process according to claim 8, wherein sources of assimilable carbon, nitrogen and/or phosphorus is/are added during the fermentation.

11. A process for preparing and subsequently therapeutically administering HMG-CoA inhibitors defined by the following formula (I)

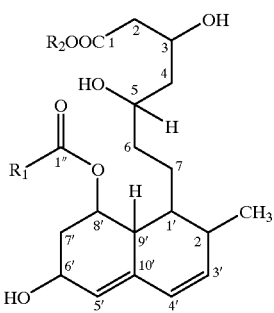

(I)

wherein $R_1$ represents substituted or unsubstituted alkyl or substituted or unsubstituted aryl, and $R_2$ independently represents H, substituted or unsubstituted alkyl or a cation;

or the corresponding lactone (II)

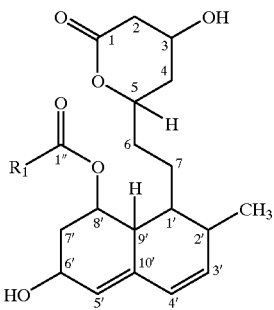

(II)

wherein $R_1$ is defined above;
which process comprises contacting a 6'-H analogue of the above formula (I) or (II) for hydroxylation with a microorganism of the species *Amycolaptosis orientalis*;
wherein the compound is administered for the prevention and/or treatment of diseases.

12. A process according to claim 2 wherein:
a. $R_1$ is an unsubstituted alkyl having a formula, $H_3C$—$CH_2$—$CH(CH_3)$, and a configuration of:

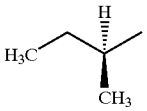

and
b. $R_2$ represents H:
and
wherein the microorganism is of the strain ATCC 19795;
wherein the analogue is added to the fermentation broth in a batch, fed-batch or continuous manner;
wherein the analogue is added to the medium to the final content of 0.05 to 0.5 wt. % based on the total medium weight; and
wherein the sources of assimilable carbon, nitrogen, and/or phosphorous is/are added during the fermentation.

* * * * *

UNITED STATES PATENT AND TRADEMARK OFFICE
CERTIFICATE OF CORRECTION

PATENT NO. : 6,365,382 B1
DATED : April 2, 2002
INVENTOR(S) : Saso Kranjc et al.

It is certified that error appears in the above-identified patent and that said Letters Patent is hereby corrected as shown below:

Column 7,
Line 53, replace "sand" with -- said --.

Signed and Sealed this

Second Day of July, 2002

Attest:

JAMES E. ROGAN
Attesting Officer    Director of the United States Patent and Trademark Office